United States Patent [19]

Khuri et al.

[11] Patent Number: 5,308,315
[45] Date of Patent: May 3, 1994

[54] METHOD FOR DETERMINING THE ADEQUACY OF DIALYSIS

[75] Inventors: Raja N. Khuri, 122 Longmeadow Rd., Greenville, N.C. 27858; Nazih L. Nakhoul, Greenville, N.C.

[73] Assignee: Raja N. Khuri, Greenville, N.C.

[21] Appl. No.: 98,119

[22] Filed: Jul. 27, 1993

[51] Int. Cl.$^5$ .............................................. A61M 1/16
[52] U.S. Cl. ........................................ 604/4; 210/646
[58] Field of Search ........................................ 604/4–6, 604/65, 66; 210/646, 647, 327.71

[56] References Cited

U.S. PATENT DOCUMENTS

| | | | |
|---|---|---|---|
| 4,647,378 | 3/1987 | Minami | 210/646 |
| 5,230,702 | 7/1993 | Lindsay et al. | 604/4 |

OTHER PUBLICATIONS

Gotch et al., A mechanistic analysis of the National Cooperative Dialysis Study (NCDS); Kidney Internat. 28:526–534 (1985).

Aebischer et al., Comparison of Urea Kinetics and Direct Dialysis Quantification in Hemodialysis Patients; Trans. Am. Soc. Artif. Intern. Organs XXXI:338–341 (1985).

Daugirdas, The post:pre dialysis plasma urea nitrogen ratio to estimate K.t/V and NPCR: validation. Int. J. Artif. Organs 12:411–419 (1989).

Garred et al., Urea kinetic Modelling by partial dialysate collection, Int. J. Artif. Organs 12:96–102 (1989).

Brunner et al., Results of Renal Replacement Therapy in Europe, 1980 to 1987, Am. J. Kidney Dis. SV:384–396 (1990).

Lowrie et al., The Urea Reduction Ratio (URR)-A Simple Method for Evaluating Hemodialysis Treatment, Contemp. Dialysis & Nephrol., Feb. 1991:11–19.

Shaldon et al., Survival and Adequacy in Long-Term Hemodialysis, Nephron 59:353–357 (1991).

Vanholder et al., Adequacy of dialysis: A critical analysis, Kindey Internat. 42:540–558 (1992).

Hakim et al., Adequacy of Hemodialysis, Amer. J. Kidney Dis. XX:107–123 (1992).

Keshaviah et al., Clinical Evaluation of a New On-line Monitor of Dialysis Adequacy, J. Amer. Soc. Nephrol. 3:374 (Nov. 1992).

*Primary Examiner*—Lee S. Cohen
*Assistant Examiner*—Robert L. Nasser, Jr.
*Attorney, Agent, or Firm*—Olive & Olive

[57] ABSTRACT

A method for determining the adequacy of dialysis, using determination of urea concentration in the dialysate effluent with an enzymatic urease sensor, and conversion of this information to arterial urea nitrogen utilizing a flow ratio correction; and utilizing the arterial blood urea nitrogen derived from readings of an on-line monitoring sensor as an absolute quantity, and the urea reduction ratio as a relative quantity as a new end-point for dialysis adequacy.

2 Claims, No Drawings

METHOD FOR DETERMINING THE ADEQUACY OF DIALYSIS

BACKGROUND OF THE INVENTION

1. Field of the Invention

This invention relates to a method of monitoring dialysis patients to ensure that there is adequate dialysis.

2. Description of the Related Art

Dosimetry of dialytic treatment of end-stage renal disease (ESRD) is traditionally specified in terms of time or duration of dialysis. Like the elevation of blood pressure in hypertension or the elevation of sugar in diabetes, ESRD manifests itself with elevation of retention products. Although there is no ideal marker to represent uremic toxins, urea is the best marker, and currently the goal of dialysis is primarily aimed at clearance of urea. Urea level is subject not only to urea removal by dialysis in ESRD, but also to urea generation by protein catabolism and the level of protein intake. A high blood urea nitrogen (BUN) is generally accompanied by increased morbidity. Middle-sized molecules such as vitamin $B_{12}$ and larger molecules like parathormone (PTH) and $\beta_2$ microglobulins have yielded poor correlations with adequate dialysis. Thus, dialysis therapy is geared toward the reduction of urea and other uremic toxins so that their concentrations approach almost normal level.

Use of the index of time or duration of dialysis is the current method used to determine the adequacy of dialysis. This method rather than prescribing a particular dosage of treatment can present problems for patients whose reaction to dialysis does not follow the predicted pattern. Recent studies have pointed to the use of time as an end-point in dialysis therapy as a main factor in the high mortality rates for dialysis in the United States, where the average treatment time is less than 12 hours per week, as compared with Japan and Europe where the average weekly treatment times are 15 and 12 hours per week, respectively. See Brunner et al., Am. J. Kidney Dis. 15:384-396, 1990.

The current methods for calculating dialysis prescription and for assuring the adequacy of dialysis treatment include such indices as KT/V (with K = dialyzer clearance, T = time of dialysis and V = volume of distribution of urea, which may change due to ultrafiltration); the time average concentration of blood urea ($TAC_{urea}$), the protein catabolic rate (PCR) and the urea reduction ratio (URR). These have recently been reviewed by Hakim et al., Am. J. Kidney Dis. 20:107-124, 1992. KT/V has been calculated in the past from the equation: $KT/V = -\ln(C_t/C_o - 0.008t - UF/W)$ where $C_t$ is the postdialysis urea level and $C_o$ is the predialysis urea level; t is the time; UF is the ultrafiltrate removed; and W is the postdialysis weight (Daugirdas, JT, Int. J. Artif. Organs 12:420-427, 1988). TACurea represents an average urea concentration, and reflects exposure to the uremic toxin urea, which should generally be below 50 mg/dl for a low morbidity. The indices $TAC_{urea}$ and PCR, while serving as relevant indicators of adequacy of dialysis, cannot be used to prescribe dialysis. The methods used for defining the dialysis prescription time dose are all based on indices derived from urea studies, which involve arguably questionable assumptions and estimates, and are indirect techniques.

It is therefore an object of this invention to provide a reliable method for defining the end-point of dialysis to insure the adequacy of dialysis.

It is a further object of this invention to provide a non-invasive, accurate method of determining whether dialysis has to proceed for a sufficient time, utilizing measurements of urea concentration in the effluent dialysate.

Other objects and advantages will be more fully apparent from the following disclosure and appended claims.

SUMMARY OF THE INVENTION

The invention is a method for determining the adequacy of dialysis, comprising determination of urea concentration in the dialysate effluent with an enzymatic urease sensor. This information is converted to arterial urea nitrogen utilizing a flow ratio correction. Arterial urea nitrogen derived from readings of an on-line monitoring sensor may be utilized as an absolute quantity, or may be used to determine the relative urea reduction ratio, as an end-point for dialysis adequacy.

Other aspects and features of the invention will be more fully apparent from the following disclosure and appended claims.

DETAILED DESCRIPTION OF THE INVENTION AND PREFERRED EMBODIMENTS THEREOF

The present invention provides a method comprising utilizing electrometric measurements of urea concentration in effluent dialysate to calculate arterial blood urea nitrogen (BUN) using equations discussed below. Arterial BUN is a reliable index of the dialysis process if the protein catabolic rate is constant and adequate protein intake of 0.8-1.4 g/day is maintained in the steady-state.

In particular, the method of the invention for determining the adequacy of dialysis of a patient, comprises:
(a) providing an enzymatic urease-based sensor;
(b) using said sensor to determine the concentration of urea in dialysate from said dialysis;
(c) determining rates of venous blood flow, dialysis fluid flow and arterial blood flow;
(d) determining a flow ratio defined as the sum of said rates of venous blood flow and said dialysis fluid flow, divided by the rate of arterial blood flow;
(e) determining urea nitrogen concentration in the blood of said patient utilizing said urea concentration in dialysate and said flow ratio; and
(f) ceasing dialysis of said patient when said urea nitrogen concentration in the blood reaches a predetermined level.

The preferred method further comprises making multiple on-line measurements of the concentration of urea in said dialysate; and providing a profile of urea reduction utilizing said measurements to assess the adequacy of dialysis on an ongoing basis.

Arterial blood urea nitrogen ($B_A$) is calculated using first principles of urea mass balance (urea entering dialyzer = urea leaving dialyzer) and dialysate urea concentration measurements ($D_U$). Urea mass balance may be expressed as follows:

$$Q_A = Q_D + Q_D$$

where Q = quantity per unit time; A = arterial; V = venous; and D = dialysate effluent.

Each of the terms of this equation is equivalent to the relevant flow rate multiplied by the relevant concentration as follows:

$$BF_A \times B_A = (BF_V \times B_V) + (V_D \times D_U) \quad \text{(equation 1)}$$

where BFA = arterial blood flow rate in ml/min; $B_A$ = concentration of urea in arterial blood reported in urea nitrogen (mg/ml); $BF_V$ = venous blood flow rate (ml/min); $B_V$ = concentration of urea in venous blood (mg/ml); $V_D$ = flow rate of dialysis fluid (ml/min) and $D_U$ = concentration of urea in dialysate (mg/ml).

Separate actual determinations of $B_V$ and $D_U$ show that these two numbers are equal due to the presence of a diffusion equilibrium across the dialyzer. This means that the following equation can be written:

$$B_A = D_U(BF_V + V_D)/BF_A \quad \text{(equation 2)}$$

All of the terms of the "flow ratio", defined as $(BF_V + V_D)BF_A$ can be set or adjusted and Du can be measured with a urease enzyme-based sensor electrode as discussed above. Thus, $B_A$ can be determined at frequent time intervals.

Under the usual conditions for dialysis, $BF_V = 240$ ml/min; $BF_A = 250$ ml/min and $V_D = 510$ ml/min. In comparison, the ultrafiltration (removal of fluid from the blood to the dialysate during dialysis) is finite and relatively small. Thus, in the standard case, ultrafiltration may be adjusted to, for example, 2.41 (about 5.31 lb) over a period of 4 hours of dialysis. This is equivalent to 2400 ml/240 minutes or 10 ml/minute.

In the preferred embodiment of the invention a urea sensor is incorporated into the artificial kidney to continuously monitor arterial BUN in the dialysate. Such an element incorporates a urease enzyme sensor located in the dialysate effluent stream, and as such, is distal to the extracorporeal stream so that it does not contaminate the return blood flow to the patient. An ideal location for the urea sensor would be at the arterial outflow, but the urease is poisoned by the presence of blood. By using the volume flow ratio, the arterial blood urea can be reliably calculated. Thus, depending on how often the readings are taken, on-line and/or continuous calculations of arterial BUN may be done. With use of technology known in the art, on-line measurements of the concentration of urea in the dialysate ($D_U$) can be obtained, thus providing a profile of urea reduction that can be used to assess the adequacy of dialysis. A simple example of an on-line sampling port comprises a three-way connector to allow frequent sampling. Since sampling is from outgoing dialysate (towards the drain), contamination is not a risk factor.

In another embodiment of the invention, the arterial BUN calculations are used along with time of dialysis and other selected dialysis indices known in the art such as PCR and $TAC_{urea}$ to provide a more accurate measure of the adequacy of dialysis. Parameters such as KT/V and URR can be manipulated to adjust dialysis dosimetry. The KT/V of the delivered dialysis session may be determined by knowing the predialysis and postdialysis BUN. Thus, KT/V, which can be calculated by multiplying the dialyzer clearance (K) as supplied by the manufacturer, which is flow dependent, by the time of dialysis, and dividing by the volume of distribution of urea, may be predicted by the arterial BUN readings obtained according to the invention. This allows adjustment of the individual time of dialysis or trouble-shooting of problems such as inadequate effective blood flow (even at best, the arterial blood flow is gradually built up at the beginning of dialysis), dialysate flow problems, or calculations of time (interruptions due to pressure building up and the like) that may significantly reduce the amount of delivered dialysis.

Readings of BUN obtained according to the invention as derived simply from direct measurements can also be used to calculate URR which also adds another parameter to assessing the adequacy of dialysis. Whereas the individual BUN readings provide an absolute measurement and a target value, for example, <30 mg/dl, to end the dialysis session, URR provides a relative measure. This is useful in some cases where initial plasma urea concentration is relatively low, such as with low protein intake, and therefore, the individual dialysis session may be adjusted to accomplish a URR, for example, of about 65% of the target value to insure adequate dialysis.

The invention herein thus preferably includes three main components: (1) monitoring urea in dialysate effluent using an enzymatic urease sensor; (2) converting the dialysate urea nitrogen (DUN) to the simultaneous arterial urea nitrogen (BUN) by multiplying the flow ratio correction times the DUN; and (3) utilizing the BUN derived from readings of an on-line monitoring sensor directly (arterial BUN) as an absolute quantity and the urea reduction ratio as a relative quantity, which is a new end-point defining the adequacy of dialysis and to estimate or determine other dialysis parameters as discussed above.

The features and advantages of the present invention will be more clearly understood by reference to the following examples, which are not to be construed as limiting the invention.

EXAMPLES

EXAMPLE I

Patients employed in dialysis study

Four male patients, aged 35-59 years, with chronic renal failure who were on maintenance dialysis were selected. No special dietary restrictions were employed. Patients weighed 194-260 pounds. Their symptoms included chronic glomerulonephritis and primary hypertension, with diabetes mellitus in one case. The patients were dialyzed for four hours, three times a week, using a hollow fiber cellulose membrane on a Baxter SPS 550 (Terumo Company, NJ) dialysis machine.

Three experimental protocols (discussed below in more detail) were employed with the four patients. In all protocols used to study dialysis, ultrafiltration was constant and finite at 10 ml/min. Under all protocols, $D_U$ was measured at regular intervals in dialysate sampled frequently, at which time blood samples were also obtained. Values of $D_u$ were used in equation 2 above to calculate $B_A$ under the varying conditions and were also compared to $B_A$ values obtained from the corresponding plasma samples. Comparisons between treatments were performed with paired Student's t-test. A statistical significance was determined at a two-tailed p value of <0.05.

EXAMPLE II

Analysis of urea concentration

A modified NOVA 12 chemistry analyzer (Nova Biomedical, Waltham, MA), with a urease enzyme-based sensor electrode was used to measure the urea concentration electrometrically in aliquots of sampled dialysate at selected time intervals. Plasma and dialysate determinations of urea concentration using a spectrophotometric method (Abbo&t Spectrum Analyzer, Irving, TX), were also obtained from laboratory measurements on samples obtained at the same time as the samples analyzed electrometrically with the sensor. The laboratory measurements of blood and dialysate urea concentrations were used as controls to validate the calculations obtained from electrometric measurements of the dialysate urea concentrations.

EXAMPLE III

First orotocol of study

In the first protocol, the patients underwent regular dialysis with the parameters on standard conditions ($BF_A$=250 ml/min and $V_D$ =500 ml/min). All patients were started on dialysis as usual. Within the first minute, a sample of arterial blood was drawn for laboratory determination of initial arterial BUN at time zero. Although a supple of dialysate was also obtained at this time, it was discarded because of a lack of sample equilibration within this short period of time. After one hour a second sample and two dialysate samples were obtained. The blood sample and one of the dialysate samples were sent to the laboratory for urea concentration determinations using the spectrophotometric method discussed in Example II. Urea concentration from the remaining dialysate sample at each time period was read directly using the urease-based electrode. The same procedure was repeated every hour until the end of the dialysis session for a total of five samplings per patient.

The results are shown in Table 1. The differences between the calculated arterial BUN and the measured arterial BUN are not statistically significant at any time using the paired t-test.

TABLE 1

| Subject | Time | $DUN^1$ mg % | Arterial BUN mg % calculated[2] | Arterial BUN mg % measured |
|---|---|---|---|---|
| 1 | 0 | — | — | 63 |
|   | 1 | 14.2 | 42.6 | 46 |
|   | 2 | 11.8 | 35.4 | 41 |
|   | 3 | 10.3 | 30.9 | 31 |
|   | 4 | 9.2 | 27.6 | 28 |
| 2 | 0 | — | — | 68 |
|   | 1 | 16.9 | 50.7 | 50 |
|   | 2 | 13.8 | 41.4 | 42 |
|   | 3 | 11.5 | 34.5 | 34 |
|   | 4 | 10.0 | 30.0 | 30 |
| 3 | 0 | — | — | 82 |
|   | 1 | 20.2 | 60.6 | 57 |
|   | 2 | 14.4 | 43.2 | 43 |
|   | 3 | 12.1 | 36.3 | 35 |
|   | 4 | 10.0 | 30.0 | 29 |
| 4 | 0 | — | — | 63 |
|   | 1 | 15.3 | 45.9 | 49 |
|   | 2 | 11.8 | 35.4 | 42 |
|   | 3 | 11.0 | 33.0 | 36 |
|   | 4 | 9.3 | 27.9 | 28 |

[1] Dialysate urea nitrogen measured electrometrically.
[2] A flow ratio of 3 was used (flow ratio = ($BF_1$ + $V_D$)/$BF_A$ = (240 + 510)/250 = 3).

EXAMPLE IV

Second protocol

In the second protocol, the patients were started with an initial $BF_A$ of 150 ml/min. which was then gradually increased by an increment of 50 ml/min every thirty minutes to a maximum of 350 ml/min. $V_D$ was kept constant at 500 ml/min. Manipulation of the arterial flow; rate is clinically useful in order to reduce the initial urea reduction rate, and to prevent adverse reactions to fast reductions of systemic urea concentration which are not usually matched by concomitant decreases in urea concentration in the cerebrospinal fluid. This protocol allowed checking of whether reliable values of arterial BUN may be obtained from dialysate measurements of urea concentrations even when arterial flow rates are changed.

The results are shown in Table 2. The differences between the calculated arterial BUN (from dialysate) and the measured arterial BUN (in plasma) are not statistically significant in any subject at any sampling time using the paired t-test.

TABLE 2

| Subject | Time | $BF_A$ ml/min | $FR^2$ mg % | $DUN^1$ mg % | Art. BUN mg % calc. | Art. BUN mg % meas. |
|---|---|---|---|---|---|---|
| 1 | 0 | initial | — | — | — | — |
|   | 1.0 | 150 | 4.33 | 12.8 | 54.6 | 48 |
|   | 1.5 | 200 | 3.50 | 13.5 | 47.3 | 45 |
|   | 2.25 | 250 | 3.00 | 13.5 | 40.5 | 39 |
|   | 3.1 | 300 | 2.67 | 12.7 | 33.9 | 34 |
|   | 3.75 | 350 | 2.43 | 10.9 | 26.9 | 27 |
| 2 | 0 | initial | — | — | — | — |
|   | 1.0 | 150 | 4.33 | 15.6 | 67.5 | 57 |
|   | 1.5 | 200 | 3.50 | 15.8 | 55.3 | 55 |
|   | 2.33 | 250 | 3.00 | 15.6 | 47.0 | 46 |
|   | 3.2 | 300 | 2.67 | 14.8 | 39.5 | 40 |
|   | 3.83 | 350 | 2.43 | 12.6 | 30.6 | 34 |
| 3 | 0 | initial | — | — | — | — |
|   | 1.0 | 150 | 4.33 | 16.5 | 71.4 | 54 |
|   | 1.45 | 200 | 3.50 | 15.0 | 52.4 | 47 |
|   | 2.15 | 250 | 3.00 | 14.3 | 42.9 | 42 |
|   | 3.0 | 300 | 2.67 | 13.5 | 36.1 | 32 |
|   | 3.67 | 350 | 2.43 | 12.6 | 30.6 | 25 |
| 4 | 0 | initial | — | — | — | — |
|   | 1.0 | 150 | 4.33 | 13.0 | 56.3 | 50 |
|   | 1.5 | 200 | 3.50 | 14.0 | 49.0 | 47 |
|   | 2.25 | 250 | 3.00 | 14.1 | 42.3 | 42 |
|   | 3.1 | 300 | 2.67 | 13.2 | 35.2 | 36 |
|   | 3.75 | 350 | 2.43 | 11.7 | 28.4 | 31 |

[1] Dialysate urea nitrogen measured electrometrically.
[2] Flow ratio

EXAMPLE V

Third protocol

In the third protocol, $BF_A$ was kept constant at 250 ml/min while $V_D$ was increased from 300 ml/min for the first period (95 min) to 475 ml/min for the second period (80 min) and finally to 650 ml/min for the last period (65 min). Samples were taken just before changing $V_D$. This protocol is another manifestation of controlling the decrease in blood urea by controlling the flow rate of the sink (in this case, the dialysate flow rate) in the hemodialysis session. Arterial BUN was again measured in plasma and compared to values of BUN calculated from electronic measurements.

Table 3 shows a summary of the results. The differences between the calculated arterial BUN and the measured arterial BUN are not statistically significant at any time using the paired t-test.

TABLE 3

| Subject | Time | VD ml/min | $FR^2$ mg % | $DUN^1$ mg % | Art. BUN mg % calc. | Art. BUN mg % meas. |
|---|---|---|---|---|---|---|
| 1 | 0 | — | — | — | — | — |
|   | 1.33 | 300 | 2.2 | 15.7 | 34.5 | 34 |
|   | 2.66 | 475 | 2.9 | 9.2 | 26.7 | 27 |
|   | 3.66 | 650 | 3.6 | 6.7 | 24.1 | 24 |
| 2 | 0 | — | — | — | — | — |
|   | 1.33 | 300 | 2.2 | 19.7 | 43.3 | 42 |
|   | 2.66 | 475 | 2.9 | 11.2 | 32.5 | 33 |
|   | 3.66 | 650 | 3.6 | 7.7 | 27.7 | 29 |
| 3 | 0 | — | — | — | — | — |

TABLE 3-continued

| Subject | Time | VD ml/min | FR² mg% | DUN¹ mg% | Art. BUN mg % calc. | Art. BUN mg % meas. |
|---|---|---|---|---|---|---|
|   | 1.33 | 300 | 2.2 | 19.7 | 43.3 | 38 |
|   | 2.58 | 475 | 2.9 | 10.9 | 31.6 | 28 |
|   | 3.58 | 650 | 3.6 | 6.3 | 22.7 | 22 |
| 4 | 0 | — | — | — | — | — |
|   | 1.33 | 300 | 2.2 | 19.2 | 42.2 | 41 |
|   | 2.58 | 475 | 2.9 | 11.3 | 32.8 | 34 |
|   | 3.58 | 650 | 3.6 | 6.9 | 24.8 | 28 |

¹Dialysate urea nitrogen measured electrometrically.
²Flow ratio

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of determining adequacy of dialysis of a patient, comprising:

(a) providing an enzymatic urease-based sensor;
   (b) using said sensor to determine the concentration of urea in dialysate from said dialysis;
   (c) determining rates of venous blood flow, dialysis fluid flow and arterial blood flow in said dialysis;
   (d) determining a flow ratio defined as the sum of said rates of venous blood flow and said dialysis fluid flow, divided by the rate of arterial blood flow;
   (e) determining urea nitrogen concentration in the arterial blood of said patient utilizing said urea concentration in said dialysate and said flow ratio;
   (f) calculating a urea reduction ratio;
   (g) utilizing the arterial blood urea nitrogen concentration as an absolute quantity and the urea reduction ratio as a relative quantity to determine dialysis adequacy; and
   (h) ceasing dialysis of said patient when said dialysis is adequate as determined in step (g).

2. The method of claim 1, wherein said method further cmprises making multiple measurements of the concentration of urea in said dialysate and calculating the arterial blood urea nitrogen and the urea reduction ratios on an ongoing basis to assess the adequacy of dialysis on an ongoing basis.

* * * * *

UNITED STATES PATENT AND TRADEMARK OFFICE
CERTIFICATE OF CORRECTION

PATENT NO. : 5,308,315
DATED : May 3, 1994
INVENTOR(S) : Raja N. Khuri and Nazih L. Nakhoul It is certified that error appears in the above-indentified patent and that said Letters Patent is hereby corrected as shown below:

Column 2, line 66, the formula should read as follows:

$$Q_A = Q_V + Q_D$$

Column 3, line 6, "BFA" should read --$BF_A$--; Column 3, line 18, "$(BF_V + V_D) BF_A$" should read --$(BF_V + V_D)/BF_A$--.

Column 5, line 12, "orotocol" should read --protocol--; Column 5, line 19, "supple" should read --sample--.

Column 8, line 19, "cmprises" should read --comprises--.

Signed and Sealed this

Thirteenth Day of September, 1994

Attest:

BRUCE LEHMAN

Attesting Officer       Commissioner of Patents and Trademarks